US011166628B2

(12) United States Patent  
Walker et al.

(10) Patent No.: US 11,166,628 B2
(45) Date of Patent: Nov. 9, 2021

(54) LARYNGOSCOPE WITH HANDLE-GRIP ACTIVATED RECORDING

(71) Applicant: PHYSIO-CONTROL, INC., Redmond, WA (US)

(72) Inventors: Robert G. Walker, Seattle, WA (US); Fred W. Chapman, Newcastle, WA (US)

(73) Assignee: Physio-Control, Inc., Redmond, WA (US)

( * ) Notice: Subject to any disclaimer, the term of this patent is extended or adjusted under 35 U.S.C. 154(b) by 252 days.

(21) Appl. No.: 16/409,301

(22) Filed: May 10, 2019

(65) Prior Publication Data

US 2019/0261844 A1 Aug. 29, 2019

Related U.S. Application Data

(63) Continuation of application No. 15/423,453, filed on Feb. 2, 2017, now Pat. No. 10,299,668.

(60) Provisional application No. 62/449,922, filed on Jan. 24, 2017, provisional application No. 62/290,195, filed on Feb. 2, 2016, provisional application No. 62/290,220, filed on Feb. 2, 2016.

(51) Int. Cl.
*A61B 1/267* (2006.01)
*A61B 1/00* (2006.01)

(52) U.S. Cl.
CPC ............ *A61B 1/267* (2013.01); *A61B 1/0002* (2013.01); *A61B 1/00039* (2013.01)

(58) Field of Classification Search
CPC .......................................... A61B 1/267–2676
See application file for complete search history.

(56) References Cited

U.S. PATENT DOCUMENTS

| 3,724,455 A | 4/1973 | Unger |
| 3,865,101 A | 2/1975 | Saper |
| 4,096,856 A | 6/1978 | Smith et al. |
| 4,947,245 A | 8/1990 | Ogawa et al. |

(Continued)

FOREIGN PATENT DOCUMENTS

| EP | 0801959 A2 | 10/1997 |
| EP | 0923961 A1 | 6/1999 |

(Continued)

OTHER PUBLICATIONS

JedMed Horus, an imaging system, Apr. 24, 2012, 2 pages.

(Continued)

*Primary Examiner* — Eduardo C Robert
*Assistant Examiner* — Michelle C Eckman
(74) *Attorney, Agent, or Firm* — Lee & Hayes, P.C.

(57) ABSTRACT

Disclosed are embodiments of a laryngoscope that facilitates targeted recording (video, or audio, or both video and audio) of time intervals associated with active laryngoscopy. In accordance with the teachings of the disclosure, a characteristic that reliably defines the interval of active laryngoscopy is used to trigger recording. One such characteristic is that the operator's hand is gripping the handle of the laryngoscope. Accordingly, preferred embodiments implement a laryngoscope having a handle so designed that when the handle is gripped by the operator's hand, recording is initiated and continued for as long as the operator's hand maintains a grip on the laryngoscope handle.

20 Claims, 5 Drawing Sheets

(56) References Cited

U.S. PATENT DOCUMENTS

| | | |
|---|---|---|
| 5,012,411 A | 4/1991 | Policastro et al. |
| 5,070,859 A | 12/1991 | Waldvogel |
| 5,078,134 A | 1/1992 | Heilman et al. |
| 5,105,821 A | 4/1992 | Reyes |
| 5,311,449 A | 5/1994 | Adams |
| 5,470,343 A | 11/1995 | Fincke et al. |
| 5,565,759 A | 10/1996 | Dunstan |
| 5,593,426 A | 1/1997 | Morgan et al. |
| 5,685,314 A | 11/1997 | Geheb et al. |
| 5,716,380 A | 2/1998 | Yerkovich et al. |
| 5,724,985 A | 3/1998 | Snell et al. |
| 5,814,089 A | 9/1998 | Stokes et al. |
| 5,827,178 A | 10/1998 | Berall |
| 5,914,585 A | 6/1999 | Grabon |
| 6,134,468 A | 10/2000 | Morgan et al. |
| 6,141,584 A | 10/2000 | Rockwell et al. |
| 6,183,417 B1 | 2/2001 | Geheb et al. |
| 6,188,407 B1 | 2/2001 | Smith et al. |
| 6,223,077 B1 | 4/2001 | Schweizer et al. |
| 6,275,737 B1 | 8/2001 | Mann |
| 6,402,691 B1 | 6/2002 | Peddicord et al. |
| 6,422,669 B1 | 7/2002 | Salvatori et al. |
| 6,441,747 B1 | 8/2002 | Khair et al. |
| 6,591,135 B2 | 7/2003 | Palmer |
| 6,771,172 B1 | 8/2004 | Robinson et al. |
| 6,957,102 B2 | 10/2005 | Silver et al. |
| 6,978,181 B1 | 12/2005 | Snell |
| 7,110,825 B2 | 9/2006 | Vaynberg et al. |
| 7,245,964 B2 | 7/2007 | Moore et al. |
| 7,570,994 B2 | 8/2009 | Tamura et al. |
| 7,736,301 B2 | 6/2010 | Webler et al. |
| 7,912,733 B2 | 3/2011 | Clements et al. |
| 7,946,981 B1 | 5/2011 | Cubb |
| 7,978,062 B2 | 7/2011 | LaLonde et al. |
| D663,026 S | 7/2012 | McGrail et al. |
| D669,172 S | 10/2012 | McGrail et al. |
| 8,715,172 B1 | 5/2014 | Girgis |
| 8,740,782 B2 | 6/2014 | McGrath |
| 8,986,204 B2 | 3/2015 | Pacey et al. |
| 9,095,298 B2 | 8/2015 | Ashcraft et al. |
| 9,283,342 B1 | 3/2016 | Gardner |
| 9,316,698 B2 | 8/2016 | McGrath et al. |
| 9,457,197 B2 | 10/2016 | Aoyama et al. |
| 9,468,367 B2 | 10/2016 | Ouyang et al. |
| 9,498,112 B1 | 11/2016 | Stewart et al. |
| 9,622,646 B2 | 4/2017 | Ouyang et al. |
| 9,821,131 B2 | 11/2017 | Isaacs |
| 9,880,227 B2 | 1/2018 | McGrath et al. |
| 9,943,222 B2 | 4/2018 | Chan |
| 2002/0022769 A1 | 2/2002 | Smith et al. |
| 2002/0116028 A1 | 8/2002 | Greatbatch |
| 2002/0116029 A1 | 8/2002 | Miller |
| 2002/0116033 A1 | 8/2002 | Greatbatch |
| 2002/0116034 A1 | 8/2002 | Miller |
| 2002/0128689 A1 | 9/2002 | Connelly |
| 2002/0128691 A1 | 9/2002 | Connelly |
| 2002/0133086 A1 | 9/2002 | Connelly |
| 2002/0133199 A1 | 9/2002 | MacDonald |
| 2002/0133200 A1 | 9/2002 | Weiner |
| 2002/0133201 A1 | 9/2002 | Connelly |
| 2002/0133202 A1 | 9/2002 | Connelly |
| 2002/0133208 A1 | 9/2002 | Connelly |
| 2002/0133211 A1 | 9/2002 | Weiner |
| 2002/0133216 A1 | 9/2002 | Connelly |
| 2002/0138102 A1 | 9/2002 | Weiner |
| 2002/0138103 A1 | 9/2002 | Mulhauser et al. |
| 2002/0138107 A1 | 9/2002 | Weiner |
| 2002/0138108 A1 | 9/2002 | Weiner |
| 2002/0138110 A1 | 9/2002 | Connelly |
| 2002/0138112 A1 | 9/2002 | Connelly |
| 2002/0138113 A1 | 9/2002 | Connelly |
| 2002/0138124 A1 | 9/2002 | Helfer |
| 2002/0143258 A1 | 10/2002 | Weiner |
| 2002/0147470 A1 | 10/2002 | Weiner |
| 2002/0177793 A1 | 11/2002 | Sherman et al. |
| 2002/0183796 A1 | 12/2002 | Connelly |
| 2002/0198569 A1 | 12/2002 | Foster |
| 2003/0028219 A1 | 2/2003 | Powers |
| 2003/0050538 A1 | 3/2003 | Naghavi et al. |
| 2003/0088275 A1 | 5/2003 | Palmer et al. |
| 2003/0100819 A1 | 5/2003 | Newman et al. |
| 2003/0212311 A1 | 11/2003 | Nova et al. |
| 2004/0049233 A1 | 3/2004 | Edwards |
| 2004/0096808 A1 | 5/2004 | Price et al. |
| 2004/0122476 A1 | 6/2004 | Wung |
| 2004/0162586 A1 | 8/2004 | Covery et al. |
| 2005/0075671 A1 | 4/2005 | Vaisnys et al. |
| 2005/0124866 A1 | 6/2005 | Elaz et al. |
| 2005/0244801 A1 | 11/2005 | DeSalvo |
| 2006/0069326 A1 | 3/2006 | Heath |
| 2006/0142808 A1 | 6/2006 | Pearce et al. |
| 2006/0167531 A1 | 7/2006 | Gertner et al. |
| 2006/0217594 A1 | 9/2006 | Ferguson |
| 2007/0106121 A1 | 5/2007 | Yokota et al. |
| 2007/0173697 A1 | 7/2007 | Dutcher et al. |
| 2007/0179342 A1* | 8/2007 | Miller .................... A61B 1/267 600/188 |
| 2008/0208006 A1 | 8/2008 | Farr |
| 2008/0294010 A1 | 11/2008 | Cooper |
| 2009/0203965 A1 | 8/2009 | Fujiyama et al. |
| 2009/0312638 A1 | 12/2009 | Bartlett |
| 2009/0318758 A1 | 12/2009 | Farr et al. |
| 2009/0322867 A1 | 12/2009 | Carrey et al. |
| 2010/0067002 A1 | 3/2010 | Ishii |
| 2010/0191054 A1 | 7/2010 | Supiez |
| 2010/0198009 A1 | 8/2010 | Farr et al. |
| 2010/0249513 A1 | 9/2010 | Tydlaska |
| 2010/0274082 A1 | 10/2010 | Iguchi et al. |
| 2010/0274090 A1 | 10/2010 | Ozaki et al. |
| 2010/0317923 A1 | 12/2010 | Endo et al. |
| 2011/0009694 A1 | 1/2011 | Schultz et al. |
| 2011/0034768 A1 | 2/2011 | Ozaki et al. |
| 2011/0054252 A1 | 3/2011 | Ozaki et al. |
| 2011/0144436 A1 | 6/2011 | Nearman et al. |
| 2011/0270038 A1 | 11/2011 | Jiang et al. |
| 2012/0320340 A1 | 12/2012 | Coleman, III |
| 2013/0018227 A1 | 1/2013 | Schoonbaert |
| 2013/0024208 A1 | 1/2013 | Vining |
| 2013/0060089 A1 | 3/2013 | McGrath et al. |
| 2013/0066153 A1 | 3/2013 | McGrath et al. |
| 2013/0123641 A1 | 5/2013 | Goldfain et al. |
| 2013/0197312 A1* | 8/2013 | Miller ................ A61B 1/00045 600/188 |
| 2013/0304142 A1 | 11/2013 | Curtin et al. |
| 2013/0304146 A1 | 11/2013 | Aoyama et al. |
| 2013/0304147 A1 | 11/2013 | Aoyama et al. |
| 2013/0308839 A1 | 11/2013 | Taylor et al. |
| 2014/0051923 A1 | 2/2014 | Mirza et al. |
| 2014/0073880 A1 | 3/2014 | Boucher et al. |
| 2014/0118517 A1 | 5/2014 | Fueki et al. |
| 2014/0160261 A1 | 6/2014 | Miller et al. |
| 2014/0272860 A1 | 9/2014 | Peterson et al. |
| 2014/0277227 A1 | 9/2014 | Peterson et al. |
| 2014/0278463 A1 | 9/2014 | Merry et al. |
| 2014/0343359 A1 | 11/2014 | Farr et al. |
| 2015/0080655 A1* | 3/2015 | Peterson ............ A61B 1/00105 600/112 |
| 2015/0109193 A1 | 4/2015 | Sly et al. |
| 2015/0112146 A1 | 4/2015 | Donaldson |
| 2015/0238692 A1 | 8/2015 | Peterson et al. |
| 2016/0022132 A1 | 1/2016 | Chan |
| 2016/0051781 A1 | 2/2016 | Issacs |
| 2016/0095506 A1* | 4/2016 | Dan .................... A61B 1/045 600/188 |
| 2016/0120394 A1 | 5/2016 | McGrath |
| 2016/0128548 A1 | 5/2016 | Lai |
| 2016/0157700 A1 | 6/2016 | Nearman et al. |
| 2016/0206188 A1 | 7/2016 | Hruska et al. |
| 2016/0206189 A1 | 7/2016 | Nearman et al. |
| 2016/0213236 A1 | 7/2016 | Hruska et al. |
| 2016/0242637 A1 | 8/2016 | Tydlaska et al. |
| 2016/0256047 A1 | 9/2016 | Newcomb |
| 2016/0345803 A1* | 12/2016 | Mallory ................ A61B 1/126 |
| 2017/0105614 A1 | 4/2017 | McWilliam et al. |

(56) References Cited

U.S. PATENT DOCUMENTS

| | | | |
|---|---|---|---|
| 2017/0215720 | A1 | 8/2017 | Walker et al. |
| 2017/0291001 | A1 | 10/2017 | Rosenblatt et al. |
| 2017/0300623 | A1 | 10/2017 | Rosenblatt et al. |
| 2017/0304572 | A1 | 10/2017 | Qiu |
| 2018/0020902 | A1 | 1/2018 | Merz et al. |
| 2018/0078318 | A1 | 3/2018 | Barbagli |
| 2018/0263647 | A1 | 9/2018 | Aljuri et al. |

FOREIGN PATENT DOCUMENTS

| | | |
|---|---|---|
| EP | 1228782 | 8/2002 |
| EP | 1250944 | 10/2002 |
| KR | 100969510 | 7/2010 |
| WO | WO0070889 A1 | 11/2000 |
| WO | 0166182 | 9/2001 |
| WO | 02056756 | 7/2002 |
| WO | WO02060529 A2 | 8/2002 |
| WO | 03009895 | 6/2003 |
| WO | WO2004093979 A1 | 11/2004 |
| WO | WO2005058413 A2 | 6/2005 |
| WO | WO2005058416 A1 | 6/2005 |
| WO | WO2013/056194 A1 | 4/2013 |
| WO | 2013071153 | 5/2013 |
| WO | 2014004905 | 1/2014 |

OTHER PUBLICATIONS

Office Action for U.S. Appl. No. 10/583,209, dated Oct. 19, 2010 (9 pp).
Response to Office Action for U.S. Appl. No. 10/583,209, dated Dec. 20, 2010 (8 pp).
Office Action from U.S. Appl. No. 10/583,209, dated Mar. 16, 2010, 10 pp.
Response to Office Action dated Mar. 16, 2010, from U.S. Appl. No. 10/583,209, filed Jun. 16, 2010, 17 pp.
Office Action from U.S. Appl. No. 10/583,175, dated Apr. 29, 2010, 8 pp.
Response to Office action dated Apr. 29, 2010, from U.S. Appl. No. 10/583,175, filed Jul. 29, 2010, 13 pp.
Office Action from U.S. Appl. No. 10/583,175, dated Oct. 2, 2009, 14 pp.
Response to Office Action dated Oct. 2, 2009, from U.S. Appl. No. 10/583,175, filed Jan. 4, 2010, 14 pp.
International Preliminary Report on Patentability from international application No. PCT/US2004/012421, dated Oct. 28, 2005, 6 pp.
International Search Report and Written Opinion from international application No. PCT/US2004/012421, dated Sep. 13, 2004, 7 pp.
International Search Report and Written Opinion from international application No. PCT/US2004/042376, dated Mar. 24, 2005, 7 pp.
International Preliminary Report on Patentability from international application No. PCT/US2004/042376, dated Jun. 20, 2006, 6 pp.
International Search Report and Written Opinion from international application No. PCT/US2004/042792, dated Jul. 20, 2005, 12 pp.
International Preliminary Report on Patentability from international application No. PCT/US2004/042792, dated Jun. 20, 2006, 8 pp.
Office Action for U.S. Appl. No. 16/572,120, dated Jan. 1, 2021, 9 pages.
Office Action from U.S. Appl. No. 10/583,176, dated Jan. 16, 2013, 6 pp.
Office Action for U.S. Appl. No. 11/256,275, dated Jan. 6, 2009, 8 pages.
Office Action for U.S. Appl. No. 14/069,021, dated Jan. 7, 2019, 9 pages.
Office Action for U.S. Appl. No. 10/583,209, dated Oct. 19, 2010, 9 pages.
Office Action for U.S. Appl. No. 14/069,021, dated Oct. 21, 2014, 9 pages.
Office Action for U.S. Appl. No. 14/310,841, dated Nov. 1, 2016, 13 pages.
Office Action for U.S. Appl. No. 14/069,021, dated Nov. 16, 2017, 11 pages.
Office Action for U.S. Appl. No. 10/583,176, dated Nov. 17, 2011, 7 pages.
Office Action from U.S. Appl. No. 10/583,175, dated Nov. 22, 2013, 8 pp.
Office Action for U.S. Appl. No. 13/103,783, dated Nov. 28, 2011, 7 pages.
Office Action for U.S. Appl. No. 13/965,667, dated Nov. 5, 2013, 8 pages.
Office Action for U.S. Appl. No. 15/245,450, dated Dec. 15, 2017, 8 pages.
Office Action for U.S. Appl. No. 14/069,021, dated Dec. 2, 2015, 7 pages.
Office Action for U.S. Appl. No. 13/103,783, dated Feb. 1, 2013, 8 pages.
Office Action for U.S. Appl. No. 14/491,669, dated Feb. 15, 2019, 10 pages.
Office Action for U.S. Appl. No. 15/829,660, dated Feb. 18, 2020, 12 pages.
Office Action from U.S. Appl. No. 10/583,175, dated Feb. 28, 2013, 18 pp.
Office Action for U.S. Appl. No. 13/965,667, dated Feb. 28, 2014, 8 page.
Office Action for U.S. Appl. No. 11/256,275, dated Feb. 3, 2010, 10 pages.
Office Action for U.S. Appl. No. 11/256,275, dated Feb. 3, 2011, 10 pages.
Office Action for U.S. Appl. No. 14/310,841, dated Feb. 8, 2016, 11 pages.
Office Action for U.S. Appl. No. 10/583,209, dated Mar. 16, 2010, 10 pages.
Office Action for U.S. Appl. No. 14/069,021, dated Mar. 23, 2015, 7 pages.
Office Action for U.S. Appl. No. 14/069,021, dated Mar. 9, 2017, 10 pages.
Office Action from U.S. Appl. No. 10/583,176, dated May 1, 2012, 6 pp.
Office Action for U.S. Appl. No. 15/423,453, dated May 18, 2018, Walker, "Laryngoscope With Handle-Grip Activated Recording," 8 pages.
Office Action for U.S. Appl. No. 10/583,176, dated May 20, 2011, 8 pages.
Office Action for U.S. Appl. No. 14/069,021, dated Jun. 14, 2018, 8 pages.
Office Action for U.S. Appl. No. 11/256,275, dated Jun. 9, 2008, 5 pages.
Office Action for U.S. Appl. No. 11/256,275, dated Jun. 9, 2009, 10 pages.
Office Action for U.S. Appl. No. 15/245,450, dated Jul. 13, 2018, 5 pages.
Office Action from U.S. Appl. No. 10/583,175, dated Jul. 29, 2013, 15 pp.
Office Action for U.S. Appl. No. 15/829,660, dated Jul. 30, 2019, 19 pages.
Office Action for U.S. Appl. No. 14/310,841, dated Jul. 7, 2016, 13 pages.
Office Action for U.S. Appl. No. 14/491,669, dated Aug. 29, 2019, 8 pages.
Office Action for U.S. Appl. No. 14/498,735, dated Sep. 15, 2015, 8 pages.
International preliminary report on patentability from international application No. PCT/US2004/042377, dated Dec. 17, 2004, 6 pp.
International Search Report and Written Opinion from international application No. PCT/US2004/042377, dated Dec. 17, 2004, 5 pp.

* cited by examiner

LARYNGOSCOPE WITH HANDLE-GRIP ACTIVATED RECORDING

CROSS REFERENCE TO RELATED APPLICATIONS

This patent application is a continuation of U.S. application Ser. No. 15/423,453, filed Feb. 2, 2019, which will issue as U.S. Pat. No. 10,299,668, on May 28, 2019, which claims the benefit of and priority to U.S. Provisional Patent Application Ser. No. 62/290,220 filed on Feb. 2, 2016, entitled "Laryngoscope With Handle-Grip Activated Video/Audio Recording," the benefit of and priority to U.S. Provisional Patent Application Ser. No. 62/449,922 filed on Jan. 24, 2017, entitled "Laryngoscope With Changeable Blade Shape And Size," and the benefit of and priority to U.S. Provisional Patent Application Ser. No. 62/290,195 filed on Feb. 2, 2016, entitled "Carbon Monoxide (CO) Environmental Monitoring on an Emergency Medical Device, Monitor or Defibrillator" the disclosures of which are all hereby incorporated by reference for all purposes. The present disclosure is further related to prior-filed U.S. patent application Ser. No. 14/491,669 field on Sep. 19, 2014, entitled "Multi-Function Video System," and to prior-filed U.S. patent application Ser. No. 11/256,275 filed Oct. 21, 2005, entitled "Defibrillator/Monitor System having a Pod with Leads Capable of Wirelessly Communicating," the disclosures of which are hereby incorporated by reference for all purposes.

TECHNICAL FIELD

The disclosed subject matter pertains generally to the area of medical devices, and more specifically to the area of video laryngoscopy.

BACKGROUND INFORMATION

Many medical instruments rely on the skill of the caregiver for proper use. To enhance those skills, some medical instruments may be provided with one or more features that give the caregiver more feedback on how well the caregiver is using the medical instrument. One feedback feature that has been popularized with laryngoscopes—a tubular endoscope inserted into the larynx through the mouth to observe the interior of the larynx—is a video camera which allows a caregiver to see and capture an image during the procedure. These video laryngoscopes as they are called are specialized laryngoscopes that provide real-time video of the airway anatomy captured by a small video camera on the blade inserted into the airway. They provide a video image on a small screen on the laryngoscope device, or on the screen of a device that is connected to the laryngoscope device.

Video laryngoscopes are particularly useful for intubating "difficult airways." Although video laryngoscopes can be costly to purchase and use; they may speed up the time to successful intubation by allowing the caregiver to better see the airway during the intubation process. Video laryngoscopy is becoming more commonly used to secure an airway in both hospital and prehospital environments.

Laryngoscopy to facilitate endotracheal intubation is one of the most challenging critical care procedures widely performed in prehospital emergency medical care. Some laryngoscopes are designed with a camera or fiber optics on the blade to facilitate enhanced visualization of the target structures during laryngoscopy, and some of the video laryngoscopes allow recording of the video data stream. Such products record the entire data stream from power-on to power-off of the device (or stream that entire interval of data to an accessory recording device such as a computer). However, the data of value comprises only a (potentially very small) portion of the entire recorded data stream. The excess data recorded is undesirable because it increases file size and memory requirements, necessitates more time for data transfer and data review, and increases the risk of privacy concerns surrounding the content of the captured data.

There is a long-felt yet unmet need for improvements in the area of video laryngoscopes.

SUMMARY OF EMBODIMENTS

Embodiments are directed to a laryngoscope that facilitates targeted recording (video, or audio, or both video and audio) of time intervals associated with active laryngoscopy. In accordance with the teachings of this disclosure, a characteristic that reliably defines the interval of active laryngoscopy is used to trigger recording. One such characteristic is that the operator's hand is gripping the handle of the laryngoscope. Accordingly, preferred embodiments implement a laryngoscope having a handle so designed that when the handle is gripped by the operator's hand, recording is initiated and continued for as long as the operator's hand maintains a grip on the laryngoscope handle.

DETAILED DESCRIPTION

In describing more fully this disclosure, reference is made to the accompanying drawings, in which illustrative embodiments of the disclosure are shown. This disclosure may, however, be embodied in a variety of different forms and should not be construed as so limited.

Generally described, the disclosure is directed to a laryngoscope that includes a capture device and a grip sensor. The grip sensor is configured to detect that the laryngoscope is being gripped, such as by a medical care giver. In response to detecting that the laryngoscope is being gripped, data from the capture device is stored in a non-volatile manner. Specific embodiments and implementations are described below.

Initial Discussion of Operative Environment

Figure 1:
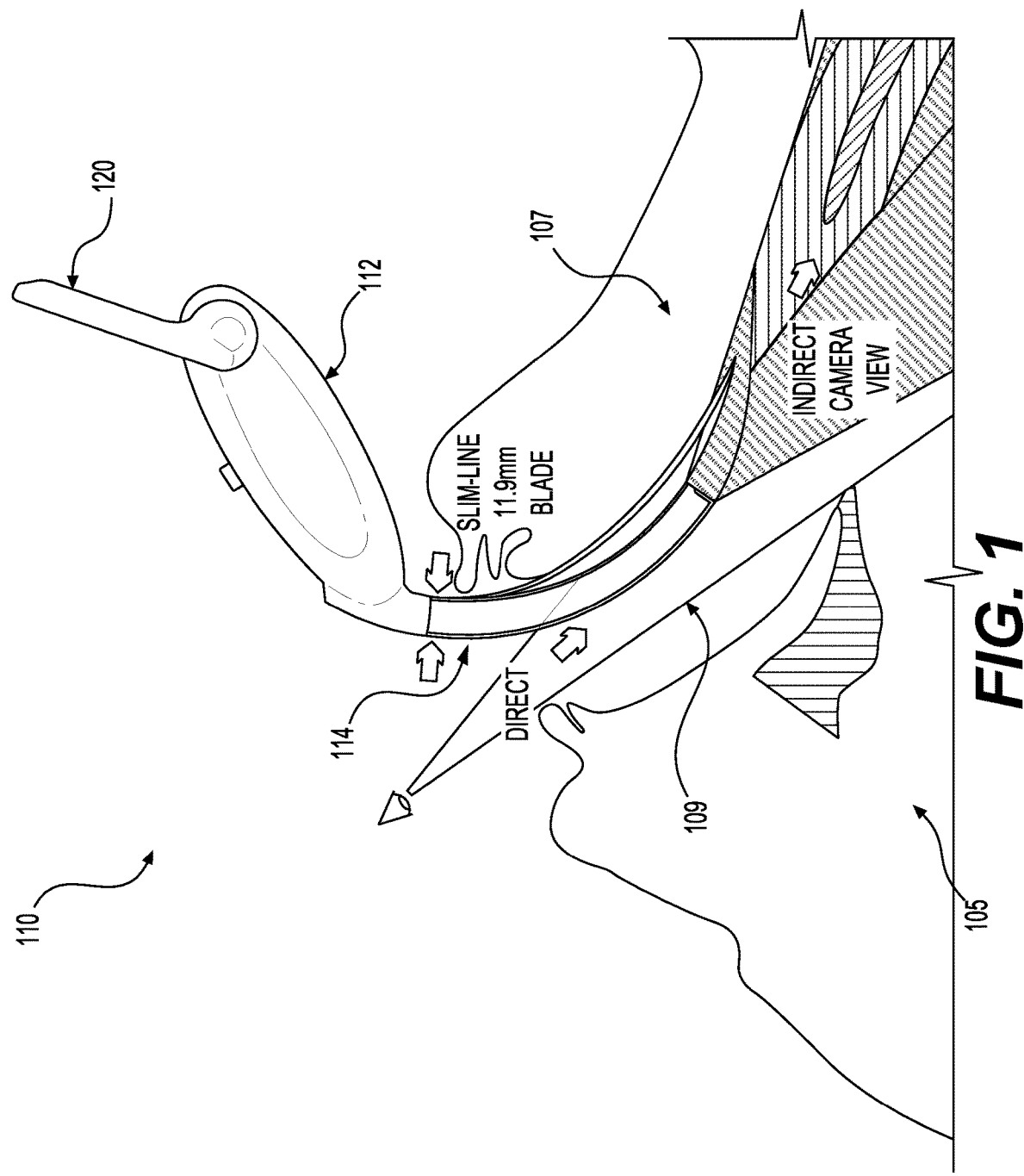
FIG. 1 is a perspective view of a video laryngoscope, according to an illustrative embodiment, in use on a patient.

FIG. 1 is a conceptual drawing that depicts an example of a patient 105 in whom a laryngoscope 110 is placed to perform a laryngoscopy. A laryngoscope is a tool used to view a patient's airway anatomy when inserting an endotracheal tube (not shown). A laryngoscopy is often performed to facilitate tracheal intubation during both elective and emergency airway management procedures in patients meeting indications for definitive airway management such as inability to adequately oxygenate or ventilate, inability to maintain airway patency or protect the airway from aspiration, or anticipation of clinical course. Tracheal intubation is the insertion of a breathing tube into the trachea for the purpose of protecting the airway and facilitating respiratory gas exchange.

The laryngoscope illustratively has a blade 107 attached by some connector mechanism 114 to a handle 112. The handle allows a caregiver to control the placement of the blade of the laryngoscope into an oral cavity 109 of the patient against the patient's tongue in connection with the laryngoscope procedure.

The laryngoscope shown in FIG. 1 is more particularly a video laryngoscope which includes a video display 120. The video display shown in FIG. 1 is illustrated as integral to the laryngoscope, although it may alternatively be connected to the laryngoscope either wirelessly or through a wired connection (not shown). The video display provides real-time video of the airway anatomy. Video laryngoscopes are used to improve visibility of the airway of the patient in order to make the task of inserting the tube easier and are particularly useful for intubating "difficult airways."

In the setting of emergency airway management, intubation is usually a time-sensitive procedure, due to risk of physiologic deterioration from the prolonged apnea resulting from lengthy intubation attempts, or due to the risk of interrupting other life-saving interventions such as chest compressions in a cardiac arrest patient or rapid evacuation and transport of a traumatically injured patient. It is therefore important to accomplish the laryngoscopy task quickly, preferably, within a single attempt. Making multiple attempts extends the period without adequate gas exchange, and consequent hypercapnia and hypoxia. For this reason, quality assurance measures are desirable to measure, monitor, and provide feedback on the timing of intubation attempts and the associated change in physiological measures (such as pulse oximetry and capnometry). The video captured by a video laryngoscope provides one form of enhanced quality assurance and quality improvement measure by providing video feedback on the procedure as it is performed, and, if the video is recorded, allowing detailed video review after the procedure is over.

Having thus introduced background on laryngoscopy, we now turn to features that are provided by this disclosure.

Figure 2:
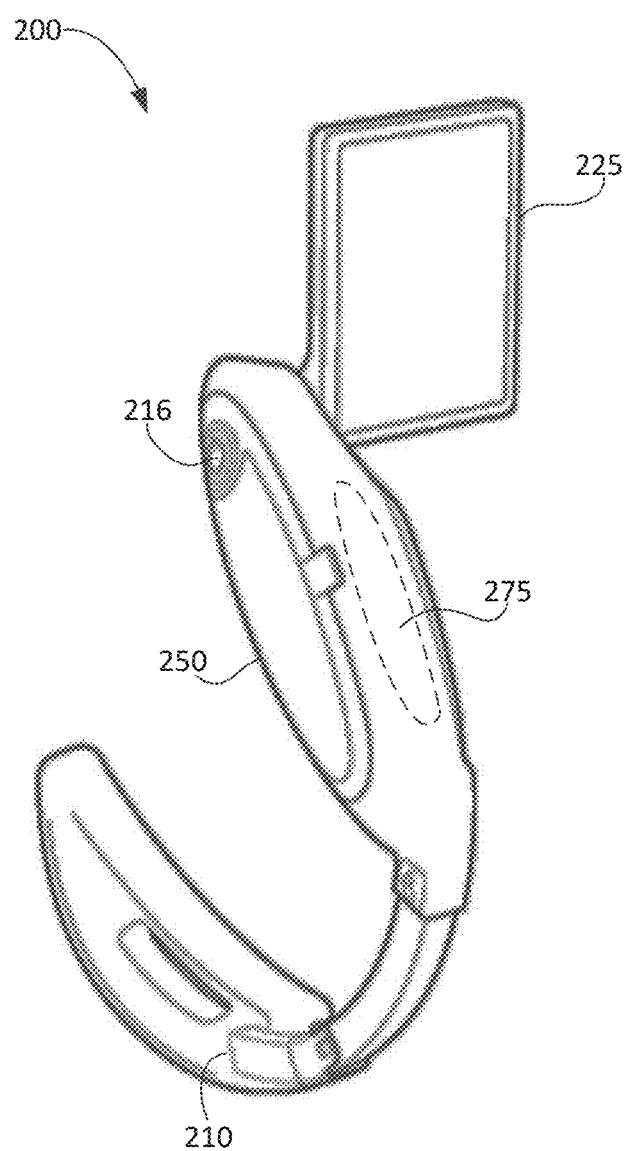
FIG. 2 is another perspective view of a video laryngoscope, according to an illustrative embodiment.

FIG. 2 is a perspective view of one embodiment of a laryngoscope 200 in accordance with the disclosure. The laryngoscope 200 includes an image capture portion 210 (e.g., a camera), a handle portion 250, and a monitor 225. Internally (so not shown), the laryngoscope 200 of this embodiment includes a processor, a memory unit, a user interface, and a communication module. These components are described in detail below in conjunction with FIG. 3. The image capture portion 210 is configured to capture one or more of a photo image, a video stream of images, or a coded image. Alternatively (or additionally), the image capture portion 210 may be configured to capture audio signals in addition to, or perhaps in lieu of, the video image(s).

The image capture portion 210 may include a light source, an image reflector unit, a window configured for diffusing light, a camera shutter, a scanner shutter, a lens system, light channels, a photodetector array, and/or a decode module. The photodetector array, in one example, may comprise a photo-sensitive charge coupled device (CCD) array that upon exposure to reflected light when enabled, generates an electrical pattern corresponding to the reflected light. Alternatively, a laser scanner and a photo-detector may be used to illustrate that different types of photodetectors besides the charge coupled photo sensitive element arrays may be used with this disclosure. As is known in the art, the light source (or a separate light source) illuminates a subject and the photodetector array converts light reflected from the subject into corresponding electrical signals. The electrical signals are in turn rendered on the monitor 225 for viewing by a user.

It should be appreciated that the image capture portion 210 may be implemented in any appropriate location or even in multiple locations. As illustrated in FIG. 2, the image capture portion 210 is integrated into the "blade" portion of the laryngoscope, but it could be implemented elsewhere, such as in the handle 250, or as a component of an attached extension, such as monitor 225. Still further, the image capture portion 210 could be located on a remote wired or wirelessly connected component of an electronic monitoring and medical care support system (e.g. a vital signs monitor, a monitor/defibrillator, a tablet device used for purposes such as documentation, or a mechanical chest compression system). Yet even further, more than one image capture portion 210 may be used and implemented in multiple locations.

Figure 5:
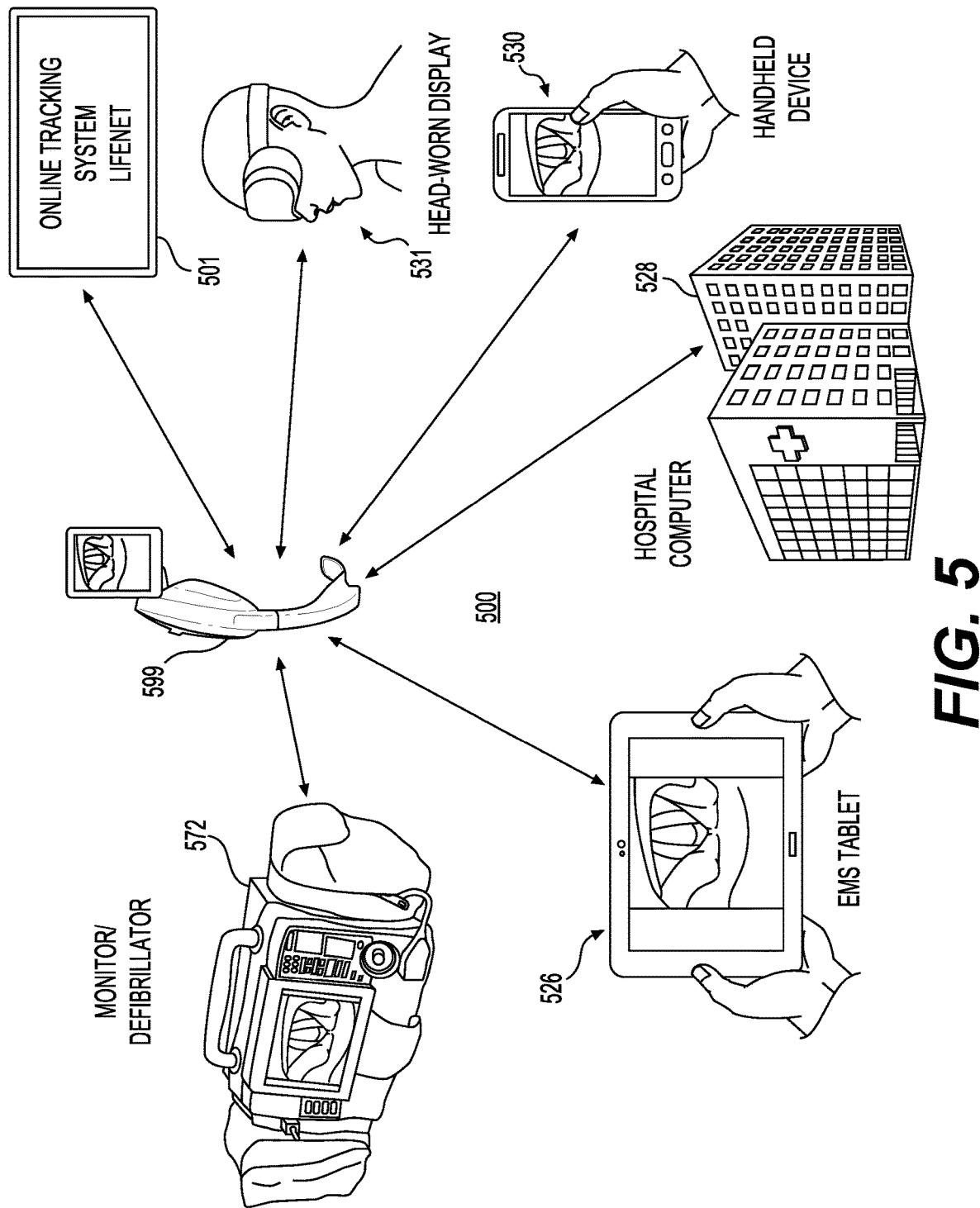
FIG. 5 is a conceptual diagram of yet another embodiment of a laryngoscope system in which components may be distributed over two or more devices, in accordance with the teachings of this disclosure.

In this embodiment, the monitor 225 is formed integral (or coupled) to the handle 250. Alternatively or in addition, the monitor 225 may take the form of a display that is separate from the handle 250. For example, the separate display may be connected to the laryngoscope 200 by a wired or wireless connection. Various monitors may be used with embodiments of this disclosure, such as an LCD screen, an e-paper (or other bi-stable) display, a CRT display, or any other type of visual display. One illustrative embodiment that uses one or more remote monitors is illustrated in FIG. 5 and described below.

The laryngoscope 200 of this particular embodiment further includes power button 216 and a grip sensor 275. The power button 216 operates to activate the laryngoscope 200 when in use and power on its various elements, e.g., the image capture portion 210, including its light source, and the monitor 225. The grip sensor 275 may be any suitable sensor that can detect that an operator is gripping the handle 250, thereby indicating that the laryngoscope 200 is in active use. The grip sensor 275 may be implemented as a pressure sensor, force sensor, temperature sensor, optical sensor, impedance (e.g., capacitive or resistive) sensor, or the like. Alternatively, the grip sensor 275 could be implemented as a tactile or electromechanical switch. In preferred embodiments, when the handle is gripped by the operator's hand (as detected by the grip sensor 275), recording is initiated and continued for as long as the operator's hand maintains a grip on the laryngoscope handle 250. Although shown in FIG. 2 as a single grip sensor 275, alternative embodiments may employ one or more grip sensors or sensor elements. Multiple grip sensors or sensor elements could be used, for example, to help differentiate the circumferential grip of a hand versus stray contact with some other object or objects. In addition, no particular significance should attach to the placement of the grip sensor 275 as shown in FIG. 2. Rather, the placement of the grip sensor 275, either on the handle 250 or elsewhere, should be viewed as a design choice with the purpose of enhancing the determination of an in-use grip by an operator versus stray contact.

In operation, an operator may handle the laryngoscope 200 in preparation for its use as described above in conjunction with FIG. 1. As part of preparing to use the laryngoscope 200, the operator will press the power button 216 to initiate the several systems of the laryngoscope 200, including the image capture portion 210 (in particular it's illuminating light source) and, perhaps, the monitor 225. At that point, the image capture portion 210 may be actively capturing and rendering images and/or video to the monitor 225. As discussed above, it may be desirable to record the images being captured by the image capture portion 210 when the laryngoscope 200 is in use. However, and also for the reasons discussed above, it may be undesirable to record all of or even a substantial portion of the images being captured. Accordingly, while in active use, an operator engages the laryngoscope 200 by holding the handle 250 in the area of the one or more grip sensors 275. The grip sensors 275 may passively determine that the laryngoscope 200 is in active use, such as by merely detecting that the operator's hand is in place in such a manner that it is likely the laryngoscope 200 is in active use. Alternatively, the grip sensor 275 may enable the operator to affirmatively indicate that the laryngoscope 200 is in active use, such as through the use of a tactile switch or the like.

In an embodiment where the image capture portion 210 is located remote to the handle 210 (e.g., wirelessly connected to a remote electronic monitoring and medical care support system), the grip sensor 275 and laryngoscope 200 may cause a signal to be sent to the remote component (not shown) to initiate recording on that remote component.

Figure 3:
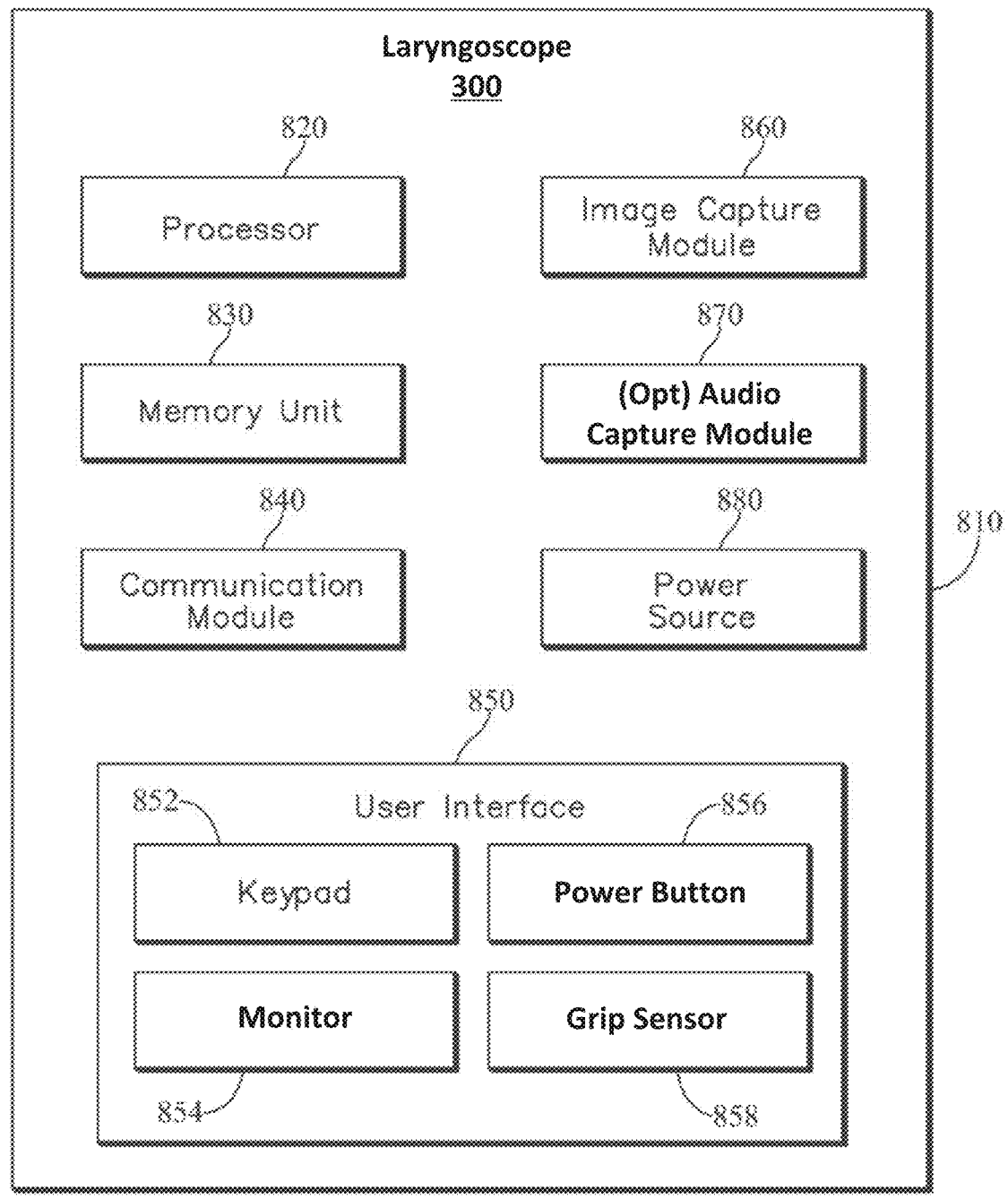
FIG. 3 is a functional block diagram generally illustrating one possible example of components of a laryngoscope according to various embodiments.

FIG. 3 is a functional block diagram 810 generally illustrating components of one particular implementation of a laryngoscope 300 constructed in accordance with this disclosure. In this embodiment, the laryngoscope 300 includes a processor 820, a memory unit 830, a communication module 840, a user interface 850, an image capture module 860, an optional audio capture module 870, and a power source 880.

Processor 820 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Memory unit 830 may be implemented in any number of ways. Such ways include, by way of example and not of limitation, volatile memory (e.g., RAM, etc.), nonvolatile memories (e.g., hard drive, solid state drive, etc.), read-only memories (e.g., CD-ROM, DVD, etc.), or any combination of these. Memory 830 may include programs containing instructions for execution by processor 820. The programs provide instructions for execution by the processor 820, and can also include instructions regarding protocols and decision making analytics, etc. In addition, memory unit 830 can store rules, configurations, data, etc. Although illustrated as being collocated with the other components of the laryngoscope 300, it should be appreciated that the memory unit 830, or an ancillary memory unit (not shown), could alternatively be located on a remote wired or wirelessly connected component.

Communication module 840 may be implemented as hardware, firmware, software, or any combination thereof, configured to transmit data between the laryngoscope 300 and other devices. In an illustrative embodiment, the communication module 840 may include a wireless module and/or a hardwire connect module. The wireless module may illustratively be a Wi-Fi module. Additionally or alternatively, the wireless module may be a Bluetooth module, a cellular communication module (e.g., GSM, CDMA, TDMA, etc.), a Wi-Max module, or any other communication module that enables a wireless communication link for the bidirectional flow of data between the image capture device and an external device. The hardwire connect module may be a hardware and software based data connector configured to connect with a data outlet of an external device such as a computer. The hardwire connect module may be implemented as one or more ports and associated circuitry and software that allow bidirectional flow of data between the laryngoscope 300 and other devices. Illustratively, the hardwire connect module may be an Ethernet connector, an RS232 connector, a USB connector, an HDMI connector, or any other wired connector. The communication module 840 is capable of enabling transmission of data captured using the image capture module 860 to other devices.

The image capture module 860 is hardware and software configured to provide the optical functionality required for the capture of photo image, a video stream of images, or a coded image. Examples of the image capture module 860 may include a complementary metal-oxide semiconductor (CMOS), N-type metal-oxide semiconductor (NMOS), a charge coupled device (CCD), an active-pixel sensor (APS), or the like. The image capture module 860 may additionally include video processing software, such as a compression/decompression module, and other components, such as an analog-to-digital converter. The image capture module 860 still further includes a light source (not shown) which is used to illuminate the subject area under view. Still further, the image capture module 860 could be implemented with additional features, such as a zooming and/or panning capability.

Although only a single image capture module 860 is shown in FIG. 3, it should be appreciated that more than one image capture module 860 could be implemented within the laryngoscope 300 or distributed among the laryngoscope 300 and other medical devices with which the laryngoscope 300 is in communication. For example, the laryngoscope 300 could have one image capture module 860 integral to the laryngoscope 300 and also be in active communication with an attachment or extension that includes a second image capture module 860.

An optional audio capture module 870 may also be included for capturing audio signals. In such an embodiment, the optional audio capture module 870 may include a microphone or other audio signal capture hardware (e.g., an analog-to-digital converter, etc.), and may also include audio processing software, such as a compression/decompression module, or the like.

The image capture module 860 and the optional audio capture module 870 could either or both be located somewhere in the body of the laryngoscope 200 (e.g., the handle, the blade, or a directly-attached extension to the laryngoscope 200, such as the monitor). Alternately or in addition, the image capture module 860 and the optional audio capture module 870 could either or both be located on a remote wired or wirelessly connected component of an electronic monitoring and medical care support system (e.g. a vital signs monitor, a monitor/defibrillator, a tablet device used for purposes such as documentation, or a mechanical chest compression system).

Power source 880 is a component that provides power to the several components of the laryngoscope 300. Power source 880 may be a battery, an externally provided power source, or a combination of both.

User interface 850 is hardware and software configured to enable an operator to interact with and control the several components of the laryngoscope 300, such as the processor 820, the memory unit 830, the image capture module 860, the communication module 840, and the optional audio capture module 870. The user interface may include a keypad 852 (either physical or virtual), a monitor 854, a power button 856 for turning on the laryngoscope 300, and a grip sensor 858 for initiating the capture of a media stream (e.g., images, video, audio, or any combination thereof). For example, user interface 850 may include a monitor 854 to display a series of instructions and a touch screen keyboard for the operator to enter data to configure the laryngoscope 300 for a particular operation.

For example, the monitor 854 may initially show a home screen with an activate virtual button to activate the capture of image data. On pressing the activate button, the monitor 854 may display a menu of instructions to navigate the operator to configure the laryngoscope 300 to the desired settings. Alternatively, the menu may pop up automatically on the screen of the display when the power button 856 is pressed.

User interface 850 may also include a speaker (not shown), to issue voice prompts, etc. User interface 850 may additionally include various other controls, such as pushbuttons, keyboards, switches, and so on, for purposes not relevant to the present disclosure.

In operation, and as discussed above, an operator may press (or otherwise trigger) the power button 856 to power on the several components of the laryngoscope 300, including the image capture module 860 (and, in particular, its illuminating light source), the processor 820, and the memory unit 830. In this way, the laryngoscope 300 is operative to begin capturing images from the image capture module 860. Additionally or alternatively, the laryngoscope 300 may also be operative to begin capturing audio from the optional audio capture module 870.

As discussed above, upon detection of the operator's grip upon the grip sensor 880, the processor 820 causes data from the image capture module 860 (and/or the audio capture module 870) to be recorded by the memory 830. Conversely, when the grip sensor 880 no longer detects the presence of the operator's grip, the processor 820 causes the data from the image capture module 860 (and/or the audio capture module 870) to cease being recorded, although the image capture module 860 may continue to stream images.

In addition, in embodiments that implement communication between the laryngoscope 300 and other devices, such as via the communication module 840, various functions and features may be distributed or duplicated at those other devices. Turning briefly to FIG. 5, an illustrative environment is shown in which a laryngoscope 599 in accordance with the teachings of this disclosure, is deployed. In this illustrative embodiment, the laryngoscope 599 includes wireless and/or wired communication to other devices. For example, the laryngoscope 599 of this embodiment may be in communication with one or more of a monitor/defibrillator 572, an EMS tablet 526, a handheld device 530, and/or a head-worn display device 531. The laryngoscope 599 may additionally be in communication with remote services, such as a remote hospital computer 528 and/or an online tracking system 501. In other embodiments, the laryngoscope 599 may be implemented as a component or pod of a modular external defibrillator system such as disclosed in aforementioned U.S. patent application Ser. No. 11/256,275 "Defibrillator/Monitor System having a Pod with Leads Capable of Wirelessly Communicating."

It will be appreciated that the laryngoscope 599 of this embodiment may be in direct communication (e.g., Bluetooth, Wi-Fi, NFC, hard-wire, etc.) with devices that are reasonably co-located with the laryngoscope 599. Alternatively, the laryngoscope 599 may be in indirect communication with other devices (e.g., hospital computer 528) through intermediary communication components. For example, the laryngoscope 599 may connect directly to the defibrillator/monitor 572, which then relays signals to the hospital computer 528.

In the embodiment illustrated in FIG. 5, it will be appreciated that signals (e.g., video or audio data) may be displayed directly on the laryngoscope 599 as well as communicated to the other devices for simultaneous display. In this example, the images being captured by the laryngoscope 599 may be conveyed to, for instance, an EMS tablet 526 in use by another medical technician on the scene. In yet another alternative, the images being captured may be conveyed from the laryngoscope 599 through to the hospital computer 528 at which those images may be reviewed by other medical personnel, such as doctors or nurses, who may be able to render real-time assistance from their remote location.

Similarly, one or more of the remote devices may include recording mechanisms for recording all or a portion of the images being conveyed by the laryngoscope 599. These and other embodiments will become apparent to those skilled in the art from a careful study of this disclosure.

Enhancements to the Data Storage Process

Figure 4:
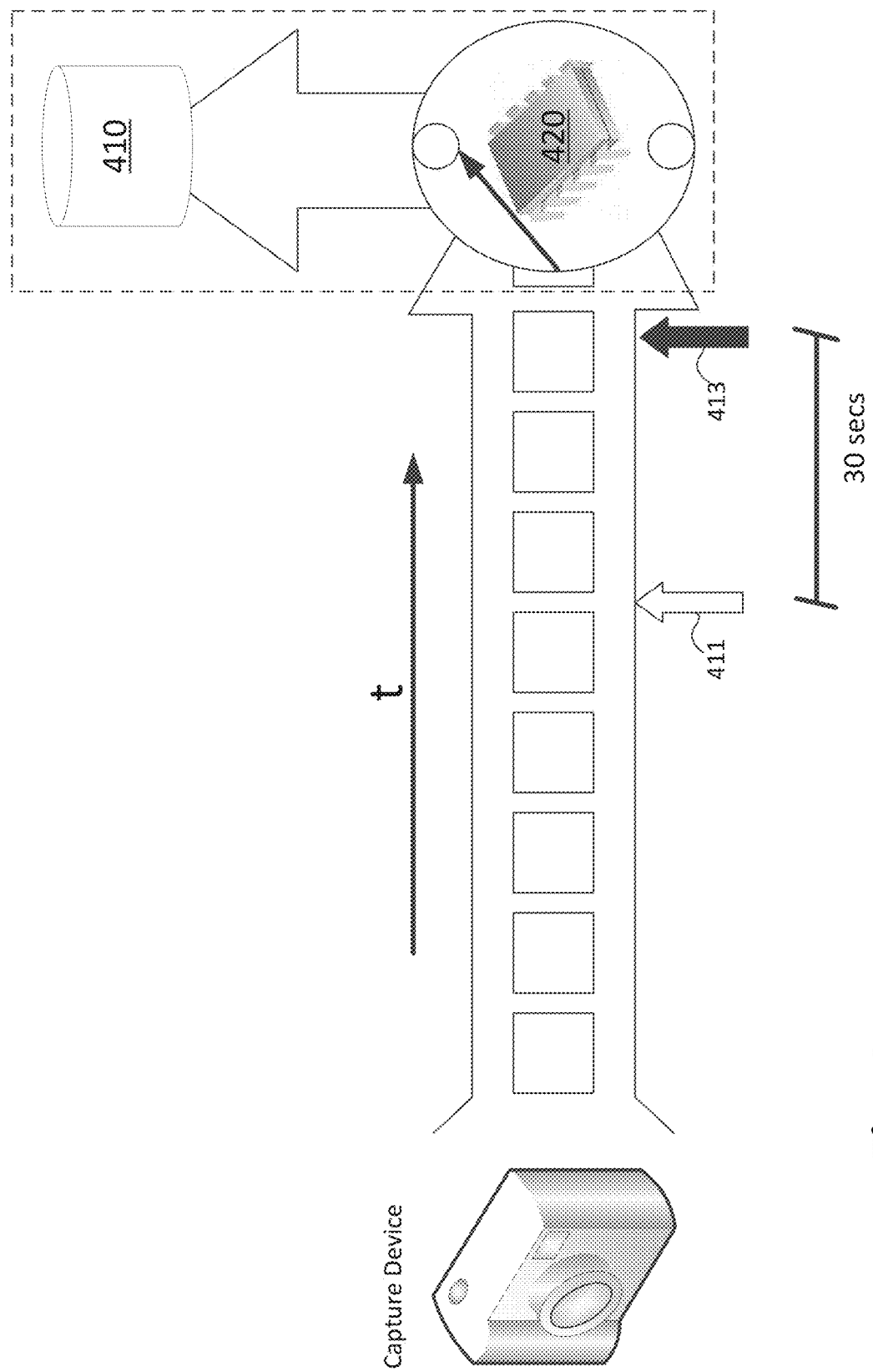
FIG. 4 is a conceptual diagram of electrical signals (e.g., video image data) being stored temporarily in a buffer for later storage in a non-volatile memory, in accordance with one embodiment.

A laryngoscope configured in accordance with the present disclosure may further include logic to enhance or simplify the capture of relevant data during a laryngoscopy while reducing irrelevant data. More specifically, it is envisioned that an operator of a video laryngoscope may be in a stressful and difficult situation, and may be occupied or preoccupied with several tasks simultaneously. To that end, it may be detrimental to the recording process if data streaming from the image capture module 860 are only recorded immediately upon activation of the grip sensor 858. For instance, an operator of the laryngoscope 300 may need to remove his or her hand briefly or readjust his or her grip on the laryngoscope 300 during operation. Embodiments of the disclosure may be implemented to address this situation. Referring now to FIGS. 3 and 4, the memory unit 830 of the laryngoscope 300 includes both non-volatile memory 410 and volatile memory 420. The volatile memory 420 includes a buffer for temporarily storing data. As shown in FIG. 4, image data being captured by the image capture module 860 is written to the volatile memory 420 and stored there temporarily for some amount of time. The duration that image data is stored will depend on many factors, including the size of the volatile memory, the pixel density of the captured images, any compression applied to the data stream, and the like. Accordingly, image data may be stored in the volatile memory 420 for some time after it is captured. The length of time image data is stored by also be field-configurable by the operator, or perhaps adjustable by the manufacturer or a service representative.

Upon the grip sensor 858 detecting the operator's grip, rather than only storing image data from that moment forward, prior image data may also be stored to non-volatile memory 410 for later use. For instance, as illustrated in FIG. 4, the grip sensor 858 may detect the operator's grip at some time "T" 41. At that instant, the processor 820 may cause image data from some configurable prior time ("T–N" 413) to be written to non-volatile memory. By way of example, the operator may grip the laryngoscope at a certain moment, thereby activating the grip sensor 858. In response, image data from the prior 30 seconds (or any other configurable time period) may be written from the volatile memory to the non-volatile memory for later use. In this way, the likelihood that relevant data is lost is decreased. For instance, should the operator release his or her grip on the laryngoscope briefly, but re-grip the laryngoscope within the configurable time frame, no image data would be lost.

In yet another enhancement, the laryngoscope 300 could be configured to continue writing image data to non-volatile memory 410 for some fixed or configurable interval of time after the grip sensor detects that the handle is no longer being gripped. Such an enhancement would further ameliorate the possibility of relevant data being lost due to brief or temporary releases of the handle.

In still another enhancement, the amount of data stored from prior-to the triggering handle-grip event, and/or after the sensor(s) detects that the handle is no longer being gripped, could be configured to be different for video vs audio data, in a system where both types of data are automatically recorded upon triggering from a handle-grip event. For example, audio data for an interval prior to and after the actual laryngoscopy may provide value for capturing details about the preparation for the procedure, and the confirmation of successful completion of the procedure, whereas video data while the operator's hand is not holding the handle is likely of no explicit value.

Additional Alternative Embodiments

Certain additional embodiments may become apparent to those skilled in the art based on the preceding disclosure. For example, one alternative embodiment may be implemented in systems in which the amount of storage space is not a constraint, yet identification of most-relevant image (or audio) data remains desirable. In such an embodiment, image data may be captured and stored to non-volatile memory for later use. In this way, the entirety of the image data stream may be available for later analysis. However, it continues to remain desirable to have easy and quick access to the most-relevant image (or audio) data recorded. Thus, the grip sensor 858 may be used to trigger the recording of a time-stamped event that is synchronized or embedded within the stream of image data. In this way, for example, a user may later quickly jump to those events (e.g., intubation, extraction, etc.) within the full recorded data stream. Still further, the grip and release events could be used to configure timing of a report of 15 intubation that, in addition to the audio or video recording, also includes physiologic data, queried from a host monitor, from a period of time related to the times of grip and release (for example, 60 seconds before grip to 180 seconds after release).

In still another alternative embodiment, a (non-video) laryngoscope may be configured with an audio loop recorder, rather than an image capture device, that captures audio data for an interval related to the grip and release times. Such an alternative embodiment would be low-cost, yet could be used in a system in which responders are trained to "talk to the device" and provide verbal comments describing the event as it progresses.

In yet another alternative embodiment, the grip sensor may be implemented in a manner that not only recognizes the presence versus absence of the operator's hand grip, but also measures the magnitude of the grip force/pressure, and/or the amount of handle surface area that is being directly contacted by the operator's hand. Such quantitative measurements could then be recorded by the laryngoscope system, allowing enhanced review and analysis of these aspects of laryngoscopy technique.

In an extension of the above embodiment, a certain pattern of applied grip pressure/force—such as, for example, two squeezes in rapid succession akin to a double mouse click on a computer—could be used to trigger recording of a discrete snapshot image, separate from the continuous video file that may also be in the process of being recorded. Such an operator-triggered snapshot image capture capability would allow the operator to capture a favorable or optimal image of interesting or noteworthy airway anatomy or airway conditions, for purposes such as documentation, education, and quality improvement. One specific use of such an operator-triggered snapshot image capture capability would be to facilitate transfer or transmission of that image by the laryngoscope system (and/or a communicatively-coupled monitor-defibrillator system) into the patient care report, the patient's medical record, or a handoff report, specifically to alert and illustrate to downstream care providers specific airway features that may make the patient more challenging to intubate. Such a "difficult airway handoff alert and illustration", forwarded from a first care provider who has already navigated a difficult airway, to a downstream care provider who may otherwise be unaware of the specific challenges posed by the particular patient's airway, would allow downstream care providers to make safer and more informed decisions about additional airway management procedures such as endotracheal tube exchange or extubation.

In yet another alternative embodiment, the grip sensor could be incorporated into a sleeve that fits over/around the handle of the laryngoscope, rather than into the handle itself. Such a sleeve could then also be used on direct (non-video) laryngoscopes as well, wherein the hand grip detected by the sensor could be used for the aforementioned tasks of initiating and terminating recording of audio data, as well as recording specific event times associated with handling of the laryngoscope.

In yet another alternative embodiment, the pressure or force sensor indicative of active use of the laryngoscope could be located elsewhere on the laryngoscope. For example, a pressure or force sensor could be incorporated into the laryngoscope blade, allowing detection of contact and lifting force applied the anterior structures of the airway. Such pressure or force detection could then be used to similarly control video and/or audio recording as in the earlier-described embodiments. The magnitude of the pressure or force could also be measured and recorded, which would be useful for analysis of laryngoscopy technique and correlation to physiologic responses to the laryngoscopy procedure. In a related embodiment, one or more pressure or force sensors could be incorporated into the rear base of the laryngoscope blade and/or handle, such that the sensors could detect force being applied to the patient's upper (maxillary) teeth, which might result in dental trauma. Detection of such dental contact force could be used to trigger an alert or alarm notifying the operator of the hazard.

In yet another alternative embodiment, one or more proximity sensors, pointed in one or more directions, could be located in or near the blade of the laryngoscope. These sensors could be used to detect entry of the blade into a confined space such as the patient's mouth, or close approach of the blade-side of the handle to the patient's face. Detection of close proximity to the face or mouth while the video laryngoscope is on could then be used to similarly control video and/or audio recording as in the earlier-described embodiments.

Other embodiments may include combinations and sub-combinations of features described above or shown in the several figures, including for example, embodiments that are equivalent to providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this disclosure, "feature" or "features" can refer to structures and/or functions of an apparatus, article of manufacture or system, and/or the steps, acts, or modalities of a method.

In the foregoing description, numerous details have been set forth in order to provide a sufficient understanding of the described embodiments. In other instances, well-known features have been omitted or simplified to not unnecessarily obscure the description.

A person skilled in the art in view of this description will be able to practice the disclosed invention. The specific embodiments disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems. The following claims define certain combinations and subcombinations of elements, features, steps, and/or functions, which are regarded as novel and non-obvious. Additional claims for other combinations and subcombinations may be presented in this or a related document.

What is claimed is:

1. A laryngoscope comprising:
an image capture module configured to capture video;
a blade;
a sensor configured to detect entry of the blade into an oral cavity of a patient;
a communication module configured to wirelessly communicate with an external device; and
a processor configured to:
cause the video to be wirelessly transmitted to the external device; and
cause the video to be stored in memory based on the sensor detecting the entry of the blade into the oral cavity.

2. The laryngoscope of claim 1, wherein the processor is further configured to cause the video to be wirelessly transmitted to the external device in real-time.

3. The laryngoscope of claim 1, wherein the video comprises a live video feed.

4. The laryngoscope of claim 1, wherein the processor is further configured to automatically cause the video to be wirelessly transmitted to the external device when the laryngoscope is in active use.

5. The laryngoscope of claim 1, wherein the processor is further configured to receive input from the external device regarding treatment of the patient with the laryngoscope.

6. The laryngoscope of claim 1, wherein the processor is further configured to receive input from a medical care provider that is remote to the laryngoscope, the input comprising real-time assistance.

7. The laryngoscope of claim 1, wherein the external device comprises a monitor-defibrillator co-located with the laryngoscope.

8. The laryngoscope of claim 1, wherein the laryngoscope is located in a pre-hospital environment and the external device is associated with a hospital environment.

9. The laryngoscope of claim 8, wherein the external device comprises an online tracking system configured to associate the video with a handoff report.

10. The laryngoscope of claim 1, wherein the processor is further configured to transmit an instruction to output an alert at the external device, the alert based on an aspect of the video.

11. The laryngoscope of claim 10, wherein the alert comprises a difficult airway handoff alert.

12. The laryngoscope of claim 1, further comprising an audio capture module configured to capture audio when the laryngoscope is in active use, wherein the processor is further configured to cause the audio to be wirelessly transmitted to the external device.

13. The laryngoscope of claim 1, wherein the processor is further configured to cause the video to be wirelessly transmitted to multiple computing devices.

14. The laryngoscope of claim 1, wherein the processor is further configured to cause the video to be wirelessly transmitted to the external device and to a remote computing network.

15. The laryngoscope of claim 1, further comprising a display, and wherein the processor is further configured to cause the video to be output on the display.

16. The laryngoscope of claim 1, wherein the image capture module is a first image capture module, and wherein the processor is further configured to cause images of the laryngoscope in active use captured by a second image capture module to be transmitted to the external device.

17. The laryngoscope of claim 16, wherein the first image capture module is integrated into the laryngoscope and the second image capture module is wirelessly coupled to the laryngoscope.

18. A laryngoscope comprising:
a blade;
a camera integrated into the blade and configured to capture images;
a sensor configured to detect entry of the blade into an oral cavity of a patient; and
a processor configured to cause the images to be stored in memory based on the sensor detecting the entry of the blade into the oral cavity.

19. The laryngoscope of claim 18, wherein the memory is part of the laryngoscope.

20. The laryngoscope of claim 18, further comprising a communication module, and wherein the memory is part of a device located remotely from the laryngoscope and wirelessly connected to the communication module.

* * * * *